United States Patent [19]
Wanek et al.

[11] Patent Number: 5,466,513
[45] Date of Patent: Nov. 14, 1995

[54] MULTI-LAYER ABSORBENT COMPOSITE

[75] Inventors: M. Chris Wanek, Marietta, Ga., now by change of name from Mary C. Batarseh; Thomas W. Van Den Bogart, Appleton, Wis.; William A. Georger, Canton, Ga.; Brendon F. Ribble, Menasha, Wis.; Billie J. Matthews, Woodstock, Ga.; Lawrence H. Sawyer, Roswell, Ga.; Frank P. Abuto, Alpharetta, Ga.; Edward E. Werner, Oshkosh, Wis.

[73] Assignee: Kimberly-Clark Corporation, Neenah, Wis.

[21] Appl. No.: 196,920

[22] Filed: Feb. 14, 1994

Related U.S. Application Data

[63] Continuation-in-part of Ser. No. 993,245, Dec. 18, 1992, Pat. No. 5,294,478.

[51] Int. Cl.$^6$ .............................. A41B 13/02; B32B 5/26; B32B 7/02
[52] U.S. Cl. .......................... 428/218; 428/283; 428/286; 428/287; 428/340; 604/378
[58] Field of Search ................................... 428/218, 283, 428/286, 287, 340; 604/378

[56] References Cited

U.S. PATENT DOCUMENTS

| | | |
|---|---|---|
| 3,805,790 | 4/1974 | Kaczmarzyk et al. . |
| 3,996,936 | 12/1976 | Widlund et al. . |
| 4,047,531 | 9/1977 | Karami . |
| 4,102,340 | 7/1978 | Mesek et al. . |
| 4,269,188 | 5/1981 | Nishizawa et al. . |
| 4,282,874 | 8/1981 | Mesek . |
| 4,333,464 | 6/1982 | Nakano . |
| 4,333,465 | 6/1982 | Wiegner . |
| 4,354,901 | 10/1982 | Kopolow ........................ 162/158 |
| 4,364,992 | 12/1982 | Ito et al. ......................... 428/283 |
| 4,480,000 | 10/1984 | Watanabe et al. ............... 428/284 |
| 4,531,945 | 7/1985 | Allison ............................ 604/378 |
| 4,560,379 | 12/1985 | Stemmler ........................ 604/368 |
| 4,673,402 | 6/1987 | Weisman et al. ............... 604/368 |
| 4,685,914 | 8/1987 | Holtman ......................... 604/368 |
| 4,699,619 | 10/1987 | Bernardin ....................... 604/378 |
| 4,710,187 | 12/1987 | Boland et al. .................. 604/385 A |
| 4,762,521 | 8/1988 | Roessler et al. ................ 604/38 SA |
| 4,770,656 | 9/1988 | Proxmire et al. ............... 604/393 |
| 4,798,603 | 1/1989 | Meyer et al. ................... 604/378 |
| 4,806,408 | 2/1989 | Pierre et al. .................... 428/76 |
| 4,834,735 | 5/1989 | Alemany et al. ............... 604/368 |
| 4,944,735 | 7/1990 | Mokry ............................ 604/385.2 |
| 4,994,037 | 2/1991 | Bernardin ....................... 604/368 |
| 5,009,650 | 4/1991 | Bernardin ....................... 604/378 |
| 5,069,676 | 12/1991 | Ito et al. ......................... 604/358 |
| 5,134,007 | 7/1992 | Reising et al. ................. 428/78 |
| 5,176,668 | 1/1993 | Bernardin ....................... 604/368 |
| 5,294,478 | 3/1994 | Wanek et al. .................. 428/218 |

FOREIGN PATENT DOCUMENTS

| | | |
|---|---|---|
| 0212618 | 3/1987 | European Pat. Off. . |
| 0343941 | 11/1989 | European Pat. Off. . |
| 0374105A2 | 6/1990 | European Pat. Off. . |
| 0378247 | 7/1990 | European Pat. Off. . |
| 0394812A1 | 10/1990 | European Pat. Off. . |
| 4024053 | 1/1992 | Germany . |
| WO90/14061 | 11/1990 | WIPO . |
| WO9211830 | 7/1992 | WIPO . |
| WO9315702 | 8/1993 | WIPO . |

OTHER PUBLICATIONS

Test Method D2101-91, "Standard Test Methods for Tensile Properties of Single Man-Made Fibers Taken from Yarns and Tows," *American Society for Testing & Materials*, pp. 571-575.

*Primary Examiner*—James C. Cannon
*Attorney, Agent, or Firm*—Thomas J. Mielke

[57] ABSTRACT

Disclosed is an absorbent structure comprising first and second surge management layers and an absorbent layer located between said first and second surge management layers. The first surge management layer comprises synthetic polymeric fibers and the second surge management layer comprises hydrophilic fibers. The density of the absorbent layer is greater than the density of the first and second surge management layers.

23 Claims, 6 Drawing Sheets

MULTI-LAYER ABSORBENT COMPOSITE

This application is a continuation-in-part of U.S. patent application Ser. No. 07/993,245 filed Dec. 18, 1992 now U.S. Pat. No. 5,294,478

BACKGROUND OF THE INVENTION

1. Field of the Invention

The present invention relates to an absorbent composite, particularly to an absorbent composite which is useful in personal care products.

2. Description of the Related Art

Personal care products for the absorption of body fluids are known. Such products include adult incontinence products, diapers, training pants, feminine care products, wound dressings and the like. As a general rule, such personal care products generally comprise an amount of a cellulosic fiber such as wood pulp fluff. Wood pulp fluff is known to be a suitable absorbent for body fluids. As a general rule, 1 gram of wood pulp fluff is able to absorb from about 5 to about 8 grams of a discharged body fluid such as urine. A personal care product such as an infant diaper, generally has an absorbent capacity of at least about 200 to 400 grams of urine. Thus, when such an infant diaper is formed from wood pulp fluff, a relatively large quantity of wood pulp fluff must be employed.

In order to reduce the amount of wood pulp fluff and the corresponding bulk of such an infant diaper, it is known to include high absorbency materials known in the art as superabsorbents. Such high absorbency materials are generally capable of absorbing at least about 10, preferably at least about 20, and up to 50 or more times their weight in water. By incorporating such high absorbency materials in infant diapers, it is possible to reduce the overall bulk of the diaper while maintaining its absolute absorbent capacity.

Nonetheless, the use of such high absorbency materials is not without problems. For example, some high absorbency materials are known to cause gel blocking. That is, as the high absorbency materials become swollen with a liquid, they form a gelatinous mass which prevents the free flow of liquid therethrough. Thus, while the high absorbency materials may be able to absorb an initial insult, subsequent insults are unable to pass through the now swollen high absorbency material. As a result, subsequent insults tend to pool and run off of the absorbent product.

Accordingly, a number of different structures have been proposed to alleviate or reduce the problems associated with incorporating high absorbency materials in personal care products.

U.S. Pat. No. 4,699,619 issued Oct. 13, 1987, to Bernardin describes a multilayer absorbent composite having a first relatively low density layer and a second relatively high density layer underlying at least a portion of the first layer. A high absorbency material (superabsorbent) is described as being located between said first and second layers.

U.S. Pat. No. 4,102,340 issued Jul. 25, 1978, to Mesek et al. is directed to a disposable article with a particulate hydrophilic polymer in an absorbent bed. Described is an absorbent pad comprising a fibrous structure having an intermediate densified layer and a layer of highly porous, loosely compacted batt on both sides of the densified layer. One of the batt layers is described as including a particulate, water-insoluble but water-swellable polymeric absorbent.

U.S. Pat. No. 4,269,188 issued May 26, 1981, to Nishizawa et al. is directed to a disposable diaper. Disclosed is a disposable diaper including an absorbent material comprising a laminate wherein a water-absorbent polymer powder is fixed between two sheets of paper. A fluff pulp layer is located on both sides of the laminate containing a water-absorbing polymer.

While the structures described in the referenced patents have often proven beneficial, they have not completely solved the problems associated with the use of high-absorbency materials. In use, the wood pulp fluff generally serves to quickly absorb a discharged body fluid. The fluid is generally held in the pores of the fluff matrix. The high absorbency material in the fluff matrix then absorbs the fluid and, in effect, dewaters the fluff matrix. That is, the fluff serves to absorb and hold surges (relatively large quantities applied relatively quickly) of body fluid until the high-absorbency material can absorb the body fluid. Moreover, many known personal care products employ high-absorbency materials in relatively low quantities. This is because the cost of such high-absorbency materials is generally greater than the cost of a material such as wood pulp fluff. It is sometimes desirable to employ a relatively high concentration of high-absorbency material when forming a personal care product. As the concentration of high-absorbency material increases in an absorbent product, the concentration of wood pulp fluff generally decreases. The high-absorbency materials are not generally able to absorb urine at the rate at which it is applied. This may lead to leakage in absorbent structures having high concentrations of absorbent materials.

It is desired to provide an absorbent structure which may contain an absorbent layer having a relatively high concentration of high-absorbency material but which absorbent structure is capable of quickly absorbing body fluids applied thereto.

SUMMARY OF THE INVENTION

The present invention concerns an absorbent structure. The structure comprises a first surge management layer, a second surge management layer, and an absorbent layer located between the first and second surge management layers. The first surge management layer comprises a fibrous web. The first surge management layer has a basis weight of from about 20 to about 200 grams per square meter and a density of from about 0.01 to about 0.12 gram per cubic centimeter. The second surge management layer comprises a fibrous web comprising hydrophilic fibers. The second surge management layer has a basis weight of from about 20 to about 350 grams per square meter and a density of from about 0.04 to about 0.25 gram per cubic centimeter. The absorbent layer comprises means for containing a high-absorbency material and from about 50 to about 100 weight percent, based on total weight of the absorbent layer, of a high-absorbency material contained by said means for containing a high-absorbency material. The absorbent layer has a basis weight of from about 200 to about 1000 grams per square meter and a density of from about 0.06 to about 0.40 gram per cubic centimeter. The density of the absorbent layer is greater than the density of the first and second surge management layer and the density of the first surge management layer is different than the density of the second surge management layer.

DETAILED DESCRIPTION OF THE INVENTION

The present invention concerns an absorbent composite. The absorbent composite comprises first and second surge management layers and an absorbent layer located between the first and second surge management layers.

The first surge management layer comprises a fibrous web. In one specific embodiment, the fibrous web comprises synthetic polymeric fibers. The fibrous webs may be formed from any fiber capable of forming a web having the physical characteristics described herein. When the fibrous web of the first surge management layer comprises synthetic polymeric fibers, the synthetic polymeric fibers may be formed from any polymeric material capable of forming fibers which fibers can be formed into a fibrous web possessing the properties of the first surge management layer as discussed herein. Suitable polymeric material from which the synthetic polymeric fibers of the first surge management layer may be formed include polyolefins, such as polyethylene, polypropylene, and the like; polyesters such as polyethylene terephthalate and the like; polyamides such as nylon 6, nylon 6,6, poly(iminocarboxylpentamethylene) and the like; acrylics, and modified cellulosic material, such as cellulose acetate; as well as mixtures and copolymers thereof.

The synthetic polymeric fibers may be formed by meltblowing, through a spunbond process, by extrusion and drawing, or other wet, dry and melt spinning methods known to those skilled in the art. The synthetic polymeric fibers from which the first surge management layer is formed may have a discrete length or may be substantially continuous. For example, if the synthetic polymeric fibers are formed by meltblowing, the fibers may be substantially continuous (few visible ends). If the fibers are formed by extrusion and drawing to produce a tow, the tow may be used as produced or cut into staple fibers having a length, for example, of from about 25 millimeters to about 75 millimeters or short cut into lengths of from about 1 millimeter to about 25 millimeters. The synthetic polymeric fibers may suitably have a maximum cross-sectional dimension of from about 0.5 micrometer to about 50 micrometers as determined by microscopic measurement using an optical microscope and a calibrated stage micrometer or by measurement from Scanning Electron photomicrographs.

The fibrous webs may be formed directly through a spunbond or meltblown process, or by carding or air-laying staple or short cut fibers. Other methods of forming fibrous webs known to those skilled in the art may be suited for use in the present invention. The web may subsequently be bonded to enhance structural integrity. Methods of bonding fibrous webs are known to those skilled in the art and include thermal bonding, point bonding, powder bonding, ultrasonic bonding, chemical bonding, mechanical entanglement, and the like. The fibers may be homogenous fibers or may be a core/sheath or side-by-side fibers known to those skilled in the art as bicomponent fibers.

The first surge management layer comprising synthetic polymeric fibers may be formed from a single type of synthetic polymeric fiber or may contain synthetic polymeric fibers formed from different polymeric materials, having different fiber lengths or maximum cross-sectional dimensions. For example, the first surge management layer may comprise a mixture of (1) bicomponent fibers having a polyethylene sheath and a polypropylene core which bicomponent fibers have a maximum cross-sectional dimension of about 20 micrometers and a length of about 38 millimeters and (2) polyester fibers (polyethylene terephthalate) having a maximum cross-sectional dimension of about 25 micrometers and a length of about 38 millimeters. Fibers 1 and 2 may be combined in a weight ratio of from 1:99 to 99:1. The fibers may be uniformly mixed or may be concentrated at opposite planar surfaces of the first surge management layer.

The first surge management layer of the present invention comprises from 0 to about 100 weight percent, suitably from about 10 to 100 weight percent, beneficially of from about 20 to 100 weight percent, preferably of from about 25 to 100 weight percent, and most preferably of from about 50 to 100 weight percent synthetic polymeric fibers. In addition to the synthetic polymeric fibers, the first surge management layer may contain from about 100 to 0 weight percent, suitably from about 90 to 0 weight percent, beneficially from about 80 to 0 weight percent, preferably from about 75 to 0 weight percent, and most preferably from about 50 to 0 percent of a nonsynthetic polymeric fiber such as wood pulp fluff, cotton linters, cotton, regenerated cellulose, and the like.

In one preferred embodiment, the first surge management material contains synthetic polymeric fibers which are formed from a polymeric material having a high wet modulus. The importance of the modulus of a material is discussed in the book "Absorbency" edited by P. K. Chatterjee (Elsevier, New York, 1985). A polymeric material will be considered to have a high wet modulus when it has a wet modulus greater than about 80 percent of its dry modulus as determined by ASTM (American Society for Testing and Materials) test method D 2101-91 using modified gauge lengths. It is often desired to form the synthetic polymeric fibers of the first surge management material from a polymeric material having a high wet modulus because such materials generally form fibrous webs which possess a relatively high degree of wet resiliency. The wet resilience of a fibrous web is related to the pore structure (while under a load) of the fibrous web. As will be discussed in greater detail below, it is often desired that the first surge management layer have a relatively high degree of wet resilience.

The pore structure (while under a load) of a fibrous structure formed from fibers of a polymeric material will, as discussed above, relate to the wet and/or dry modulus of the constituent fibers. Wet modulus of the constituent fibers should be considered for fibers that may likely be wetted during use. For the purposes of estimating the effect of load on the pore structure of a fibrous structure formed from fibers of a polymeric material the tensile modulus of the fiber which can be related to the flexural rigidity of the fiber as shown in the book "Physical Properties of Textile Fibers" by W. E. Morton and J. W. S. Hearl (The Textile Institute, London, 1975) can be used.

As a general rule, the polymeric materials from which the synthetic polymeric fibers of the first surge management layer are formed will be inherently hydrophobic. As used herein, the term "hydrophobic" describes a material which has a contact angle of water-in-air of greater than 90 degrees. The term "hydrophilic" refers to a material which has a water-in-air contact angle of less than 90 degrees. The water-in-air contact angle is suitably determined as set forth in the book "Absorbency" edited by P. K. Chatterjee (Elsevier, New York, 1985). As used herein, a polymeric material will be considered to be "inherently" hydrophobic or hydrophilic when the polymeric material, free from any surface modifications or treatments, e.g., surface active agents, spin finishes, blooming agents, etc., is hydrophobic or hydrophilic, respectively.

When the synthetic polymeric fibers of the first surge management layer are formed from a polymeric material which is inherently hydrophobic, it is often desirable to treat the fibers with a surface modifying material to render the surface of the fiber hydrophilic. For example, a surfactant may be applied to the fibers.

The first surge management material suitably has a basis weight of from about 20 to about 200, beneficially of from about 30 to about 150, and preferably of from about 35 to about 125 grams per square meter.

The first surge management material suitably has a density of from about 0.01 to about 0.12, beneficially of from about 0.015 to about 0.1, and preferably of from about 0.02 to about 0.08 gram per cubic centimeter.

The second surge management layer also comprises a fibrous web. The fibrous web of the second surge management layer comprises hydrophilic fibers. The hydrophilic materials may be inherently hydrophilic such as cellulosic fibers such as wood pulp fluff, cotton linters, and the like; regenerated cellulose fibers such as rayon; or certain nylon copolymers such as poly(pentamethylenecarbonamide) (nylon-6)/polyethylene oxide. Alternatively, the hydrophilic fibers may be hydrophobic fibers which have been treated to possess a hydrophilic surface. For example, the fibers may be formed from a polyolefin material which is subsequently coated with a surface active agent such that the fiber itself is hydrophilic as described herein. Other methods of hydrophilizing fibers formed from hydrophobic materials are known and suited for use in the present invention.

Methods of providing inherently hydrophilic fibers such as wood pulp fluff are known. So to are methods of providing regenerated cellulosic fibers such as rayon. Hydrophobic fibers which can be treated to possess a hydrophilic surface are suitably formed in the same manner and from the same materials described above in connection with the first surge management layer. If the hydrophilic fibers are hydrophobic fibers which have been treated to possess a hydrophilic surface, the fibers will suitably have a fiber length and maximum cross-sectional dimension as set forth above. If the hydrophilic fibers are inherently hydrophilic such as wood pulp fluff, rayon, cotton, cotton linters and the like, the fibers will generally have a length of from about 1.0 millimeters to about 50 millimeters and a maximum cross-sectional dimension of from about 0.5 micrometers to about 100 micrometers.

The fibrous web of the second surge management layer may be formed in the same way as set forth above in connection with the first surge management layer. The second surge management layer suitably comprises from about 10 to 100 weight percent, beneficially from about 30 to 100 weight percent, and preferably from about 55 to 100 weight percent of hydrophilic fibers, preferably inherently hydrophilic fibers. In addition to the hydrophilic fibers, the second surge management layer may contain from about 90 to 0 weight percent of a high wet modulus, preferably inherently hydrophobic fibers. The second surge management layer may be formed from a single type of hydrophilic fiber or may contain hydrophilic fibers having different compositions, lengths and maximum cross-sectional dimensions. The second surge management layer suitably comprises a greater percentage of inherently hydrophilic fibers than the first surge management layer. Specifically, the second surge management layer suitably comprises at least about 10, beneficially about 25 and preferably about 50 weight percent more inherently hydrophilic fibers than the first surge management layer when the first surge management layer comprises inherently hydrophilic fibers.

In one preferred embodiment, the second surge management layer is formed from air laid cellulosic fibers such as wood pulp fluff. Wood pulp fluff fibers are preferred for use due to their ready availability and due to the fact that the fibers are relatively inexpensive compared to synthetic polymeric fibers.

The second surge management layer suitably has a basis weight of from about 20 to about 350, beneficially of from about 50 to about 200, and preferably of from about 25 to about 150 grams per square meter.

The second surge management layer suitably has a density of from about 0.04 to about 0.25, beneficially of from about 0.06 to about 0.16, and preferably of from about 0.08 to about 0.14 gram per cubic centimeter.

An absorbent layer is located between the first and second surge management layers. The absorbent layer is in liquid communication with the first and second surge management layers. As used herein, the absorbent layer will be considered to be in liquid communication with the first and second surge management layers when a liquid can move from either the first or second surge management layer into the absorbent layer. It is not necessary that the first and second surge management layers be in direct contact with the absorbent layer. That is, additional intervening layers can appear between the surge management layers and the absorbent layer. Nonetheless, a liquid must be able to move from the first and second surge management layers, through or around any such intervening layers and into the absorbent layer. When this is possible, the first and second surge management layers will be considered to be in liquid communication with the absorbent layer.

The absorbent layer comprises means for containing a high-absorbency material, and a high-absorbency material contained by such means for containing a high-absorbency material. The high-absorbency material is present in the absorbent structure in an amount of from about 50 to about 100, preferably of from about 60 to about 95, and most preferably of from about 70 to about 90 weight percent based on total weight of the absorbent layer.

Means of containing high-absorbency materials are known to those skilled in the art. For example, the means for containing the high-absorbency material may comprise a fibrous web, a porous sponge-like material, a substrate to which the high-absorbency material is attached or adhered, multiple sheets of material between which the high-absorbency material is located, and the like. Any means of containing of the high-absorbency material is suited for use in the present invention.

As used herein, the term "high-absorbency material" refers to a water-swellable, generally water-insoluble material capable of absorbing at least about 10, desirably about 20, and preferably about 50 times or more its weight in water. The high-absorbency material may be formed from organic material, which may include natural materials such as agar, pectin, and guar gum, as well as synthetic materials such as synthetic hydrogel polymers. Synthetic hydrogel polymers include, for example, carboxymethyl cellulose, alkali metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyrridine, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the materials substantially water insoluble. Crosslinking may, for example, be by irradiation or covalent, ionic, van der Waals, or hydrogen bonding. Suitable materials are available from various commercial vendors such as the Dow Chemical Company, Hoechst Celanese Corporation, Allied Colloid Inc., and Stockhausen Inc.

The high-absorbency material may be in the form of particles, spheres, flakes, fibers, rods, films or any of a number of geometric forms. When in the form of particles or spheres, it may be desired that the particles or spheres have a maximum cross-sectional dimension of from about 10 micrometers to about 2000 micrometers, preferably from about 60 micrometers to about 1000 micrometers.

In one embodiment it is desired that the high-absorbency material have the ability to absorb a liquid while under a load. The ability of a high-absorbency material to absorb a liquid while under a load is quantified as the Absorbency Under Load (AUL) value. Specifically, the AUL value is the amount (in grams) of an aqueous solution containing 0.9 weight percent sodium chloride, a gram of the high-absorbency material can absorb in 60 minutes under a load of 0.3 pound per square inch. As a general rule, it is desired that the high-absorbency material have an AUL value of at least about 10, desirably at least about 15, and preferably at least about 25. A method by which the absorbency under load value is determined is set forth below in connection with the Examples.

The absorbent layer suitably has a basis weight of from about 200 to about 1000, beneficially of from about 250 to about 750, and preferably of from about 300 to about 500 grams per square meter. The absorbent layer suitably has a density of from about 0.06 to about 0.40, beneficially of from about 0.12 to about 0.35, and most preferably of from about 0.15 to about 0.30 gram per cubic centimeter.

The density of the absorbent layer is greater than the density of both the first surge management layer and the second surge management layer. Suitably, the density of the absorbent layer is at least about 20 percent, beneficially at least about 30 percent, and preferably at least about 40 percent greater than the density of both the first and second surge management layers. Further, the densities of both the first and second surge management layers are different. It is preferred that the densities of the first and second surge management layers differ by at least about 20 percent of the lowest density layer.

The absorbent structures of the present invention comprise at least three layers. From the above, it is clear that the three layers of the absorbent structures of the present invention all have a different density. Further, the absorbent layer has the highest density of the three. Of the remaining two layers, the first and second surge management layers, one will have an intermediate density (relative to the absorbent layer and other surge management layer) and one will have a low density compared to the other surge management layer and absorbent layer. The absorbent layer is located between the first and second surge management layers. Thus, the density of the various layers of the absorbent structure according to the present invention will be arranged in one of the following orders: lowest density, highest density, intermediate density; or intermediate density, highest density, lowest density. For the purpose of this application, density of the first surge management layer, second surge management layer and absorbent layer refers to an average density of the layer being tested. That is, a representative number of density measurements are taken across the length and width of the layer being tested. The individual density measurements are then averaged to determine the average density. The density is determined under a load of 0.05 pound per square inch (350 pascal).

The absorbent structures according to the present invention are suitable for use in disposable absorbent products such as diapers, training pants, adult incontinence products, feminine care products, wound dressings and the like. Methods of forming such absorbent products and the absorbent products formed thereby are known to those skilled in the art and are described, for example, in the following U.S. Pat. Nos.: 4,944,735 issued Jul. 31, 1990 to Mokry; 4,798,603 issued Jan. 17, 1989, to Meyer et al.; 4,710,187 issued Dec. 1, 1987, to Boland et al.; 4,770,656 issued Sep. 13, 1988, to Proxmire et al.; and 4,762,521 issued Aug.9, 1988, to Roessler et al.; as well as U.S. patent application Ser. No. 07/757,778 filed Sep.11, 1991, in the name of Proxmire et al.; and U.S. patent application Ser. No. 07/757,760 filed Sep. 11, 1991, in the name of Hanson et al.; the disclosures of which are incorporated herein to the extent they are consistent herewith.

The absorbent structures of the present invention suitably form the absorbent core of the disposable absorbent products. Such an absorbent core is suitably sandwiched between a bodyside liner, and a liquid impervious outer cover. Thus, in use, one of the surge management layers may be located between the body of the wearer and the absorbent layer, while the other surge management layer will be located such that the absorbent layer is between it and the body of the wearer. Either the first or second surge management layer can be located on the bodyside of the absorbent layer (between the absorbent layer and the body of the wearer during use).

In one embodiment of the present invention the first surge management layer is located, during use, between the absorbent layer and the body of the wearer. In this embodiment, the first surge management layer comprises from about 10 to about 100 weight percent of a synthetic polymeric fiber formed from a high wet modulus polymeric material. The web is formed such that it possesses a relatively high degree of structural integrity. For example, the web can be formed by meltblowing or may be a bonded carded web. Such materials may generally possess a relatively high degree of wet resiliency. When the first surge management layer is resilient, the fibrous web is able to maintain an open porous structure while under a load, and to resist collapse when wetted, such that it is able to receive subsequent insults.

Specifically, in one preferred embodiment, it is desired that the surge management layer located between the body of a wearer and the absorbent layer exhibits a wet resiliency factor of at least about 1.5, preferably of at least about 1.7. The wet resiliency factor is determined by compressing a wet sample of the surge management layer at a pressure of 2.0 pounds per square inch for 60 minutes and then measuring the density at the 2.0 pounds per square inch (13.19 kilopascal) loading. The sample is then measured for density at a loading of 0.2 pound per square inch. The wet resiliency factor is determined by dividing the sample density at 2.0 psi by the sample density at 0.2 psi.

When the second surge management layer is formed from more than 50 weight percent of inherently hydrophilic fibers such as wood pulp fluff, the second surge management layer may be less resilient than the first surge management material comprising synthetic polymeric fibers. When the second surge management layer is formed entirely from wood pulp fluff, the second surge management layer possesses a relatively low degree of wet resiliency.

Accordingly, in one embodiment of the present invention, the first surge management layer is located between the body of a wearer and the absorbent layer and comprises at least about 50 weight percent of a synthetic polymeric fiber. The second surge management layer is located on the opposite side of the absorbent layer and comprises at least about 55 weight percent of a cellulosic fiber such as wood pulp fluff. Both the first and second surge management layers function by holding surges of liquid applied to the absorbent structure for a period of time sufficient for the absorbent layer to desorb the surge management layers and absorb and retain the liquid. In this manner, the surge management layers are able to receive subsequent insults of liquid (surges) and again hold the liquid for a period of time sufficient for the liquid to be absorbed by the absorbent layer.

A further advantage of locating the first surge management layer between the body of a wearer and the absorbent layer is that the first surge management material, may have a relatively dry feel even after it has been wetted. This is because the first surge management layer may include synthetic polymeric fibers, is resilient and may be more easily desorbed by the absorbent layer than the second surge management layer. Thus, a relatively dry surface may be presented for contacting a wearer's skin. In contrast, the second surge management layer including cellulosic or other inherently hydrophilic fibers can have a relatively wet feel. This wet surface is located remote from the body of a wearer and is spaced therefrom by the first surge management layer and the absorbent layer.

In order to assist the second surge management layer in performing its surge management function when it is located with the absorbent layer and first surge management layer between it and the body of a wearer, it may be desired to provide a liquid applied to the first surge management layer easy access to the second surge management layer. Accordingly, it may be desired to provide the absorbent layer and/or first surge management layer with areas of reduced basis weight or holes so that a liquid applied to the first surge management layer can pass through the areas of lower basis weight or the holes quickly and reach the second surge management layer. Alternatively, it may be desired to make the first surge management layer and/or absorbent layer smaller than the second surge management layer so that if a liquid applied to the first surge management layer and/or absorbent layer runs off of that layer, it then comes into contact with the second surge management layer which is either wider and/or longer than the first surge management layer or the absorbent layer. It may also be possible to form the first surge management layer and the absorbent layer with a low mass such that a liquid applied to the first surge management layer can pass through the first surge management layer and absorbent layer without complete dissipation of kinetic energy. For example, the absorbent layer can be formed to have large free volume pathways in which free volume is maintained even after initial wetting.

In one preferred embodiment, the absorbent layer is formed from an air-laid mixture of wood pulp fluff and high-absorbency material. The high-absorbency material is contained in the air-laid wood pulp fluff. The mixture of wood pulp fluff and high-absorbency material is suitably air-laid onto a porous forming surface through which a vacuum is drawn. The porous forming surface may be a forming wire or forming drum. In order to form holes or areas of reduced basis weight in the absorbent layer, areas of the porous forming surface are blocked off so that a vacuum is not drawn therethrough. These blocked off areas correspond to the areas of reduced basis weight or holes in the absorbent layer. The blocked off areas can be arranged in essentially any pattern desired. In one embodiment, the blocked off areas are blocked off by 3-dimensional projections. For example, the areas may be blocked off by pyramidal or conically shaped projections. Alternatively, holes may be cut in the absorbent layer by methods known to those skilled in the art.

Figure 1:
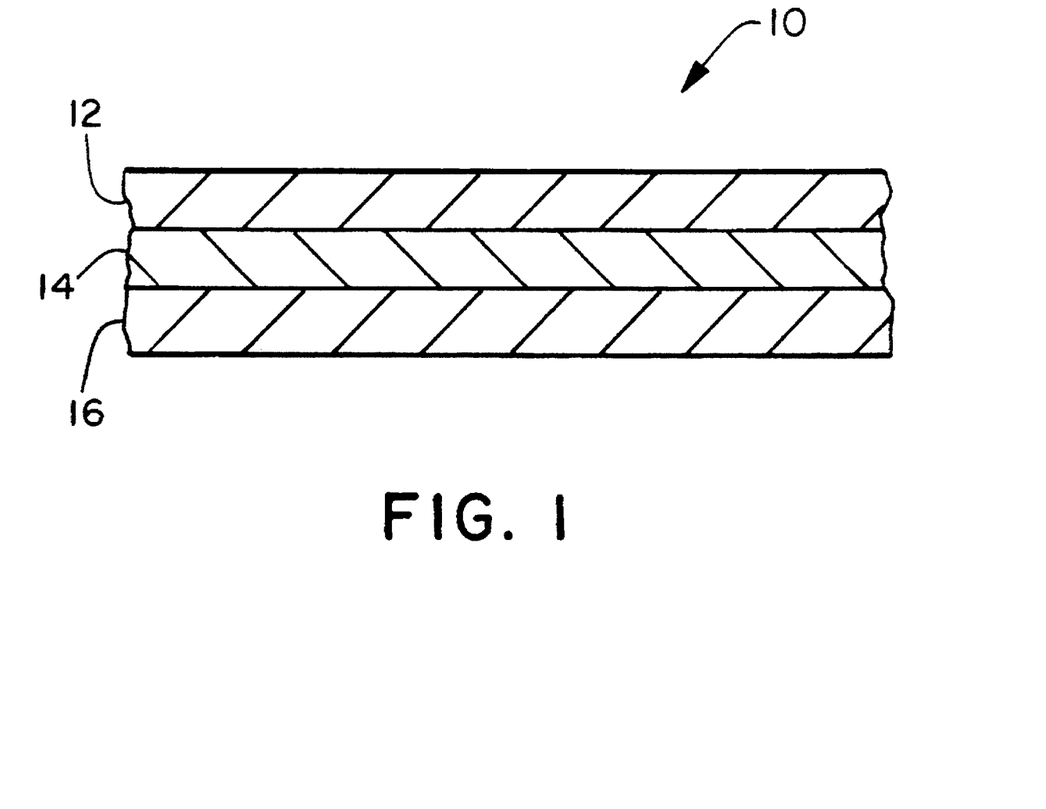
FIG. 1 is a cross-sectional view of an absorbent structure according to the present invention.

The present invention can be understood by reference to the drawings wherein FIG. 1 illustrates a cross-sectional view of the absorbent structure according to the present invention. Absorbent structure 10 comprises a first surge management layer 12, an absorbent layer 14 and a second surge management layer 16. The absorbent layer 14 is located between the first surge management layer 12 and the second surge management layer 16.

Figure 2:
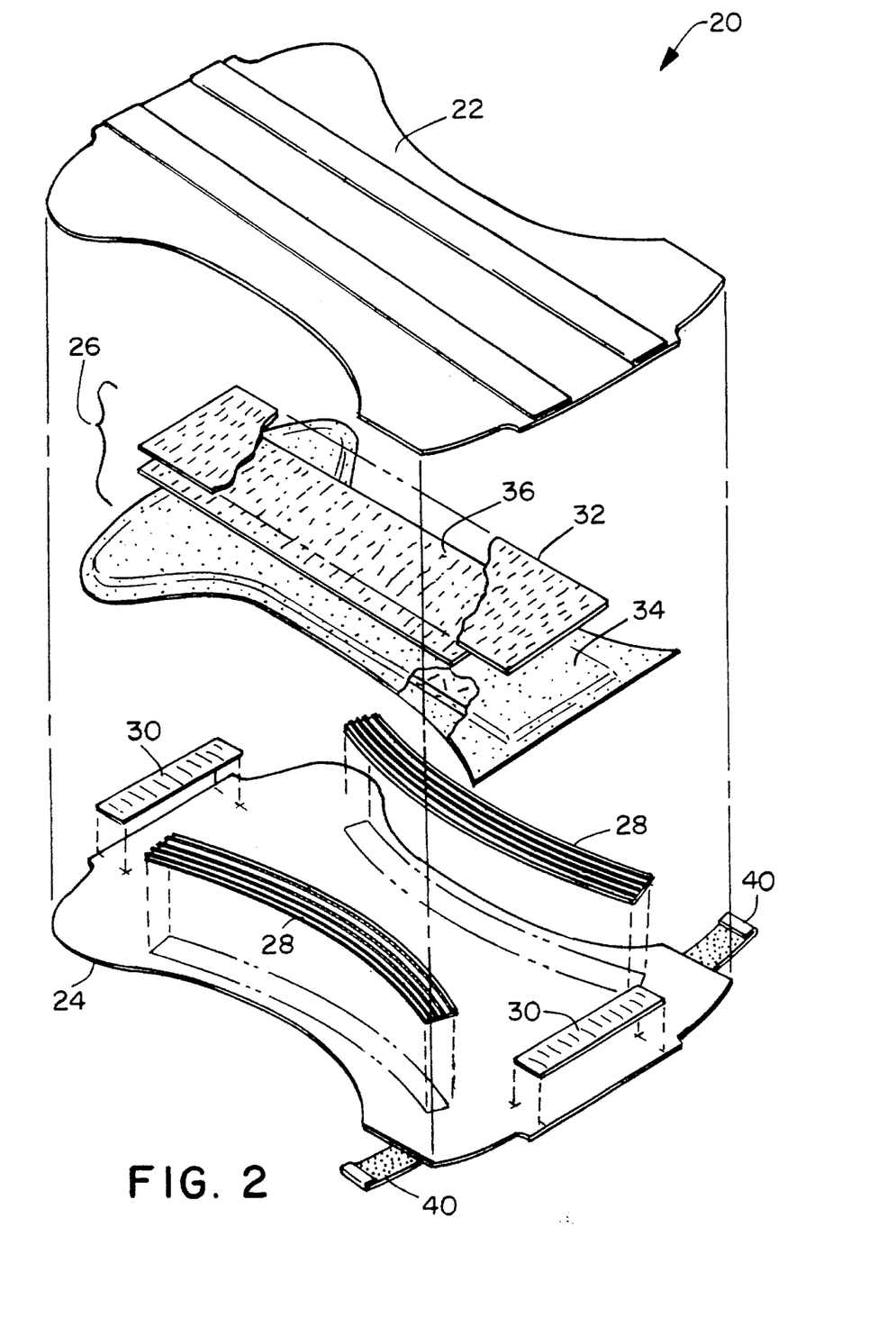
FIG. 2 is an exploded view of an infant diaper incorporating an absorbent structure according to the present invention.

As discussed above, the absorbent structures according to the present invention are suitable for use in absorbent products such as diapers. FIG. 2 illustrates an infant diaper embodying an absorbent structure according to the present invention. Diaper 20 typically includes a liquid-permeable bodyside liner 22; a substantially liquid-impermeable outer cover 24; an absorbent structure 26, positioned between the liner and outer cover; leg elastic members 28; and waist elastic members 30. The liner 22, outer cover 24, absorbent structure 26, and the elastic members 28 and 30 may be assembled in a variety of well-known diaper configurations. It should be recognized, however, that in articles other than diapers, individual components, such as the liner, outer cover, or elastic members, may be optional. The desirability of including particular components in other absorbent articles would depend on the intended end use of the absorbent article.

The absorbent structure 26 comprises a first surge management layer 32, a second surge management layer 34, and an absorbent layer 36 located between the surge management layers 32 and 34. As can be seen from reference to FIG. 2 in the illustrated embodiment, the second surge management layer 34 is larger than the absorbent layer 36 and the first surge management layer 32. Thus, if a liquid cannot be held or absorbed by the first surge management layer 32 or rapidly absorbed by the absorbent layer 36, and the liquid runs off, it will come into contact with the second surge management layer 34 and be maintained in the absorbent structure. The diaper illustrated in FIG. 2 further comprises containment flaps 38 known to those skilled in the art and adhesive tape members 40 for attaching the diaper about the waist of an infant.

Those skilled in the art will recognize materials suited for use in forming the components of the diaper illustrated in FIG. 2. Further, it is known that the components of the absorbent structure 26 may be individually or collectively wrapped in a low basis weight material such as a cellulosic wrap sheet (basis weight about 11 grams per square meter) or similar material.

If it is desired to impart the ability for the absorbent structure according to the present invention to perform a distribution function, it may be possible to provide either the first or second surge management layer with the ability to distribute a liquid. Methods of imparting the ability to distribute a liquid to fibrous webs are known. For example, when the second surge management layer is formed from wood pulp fluff, it may be possible to densify the wood pulp fluff either across its entire width or to provide densified channels which are capable of distributing a liquid.

Figure 3:
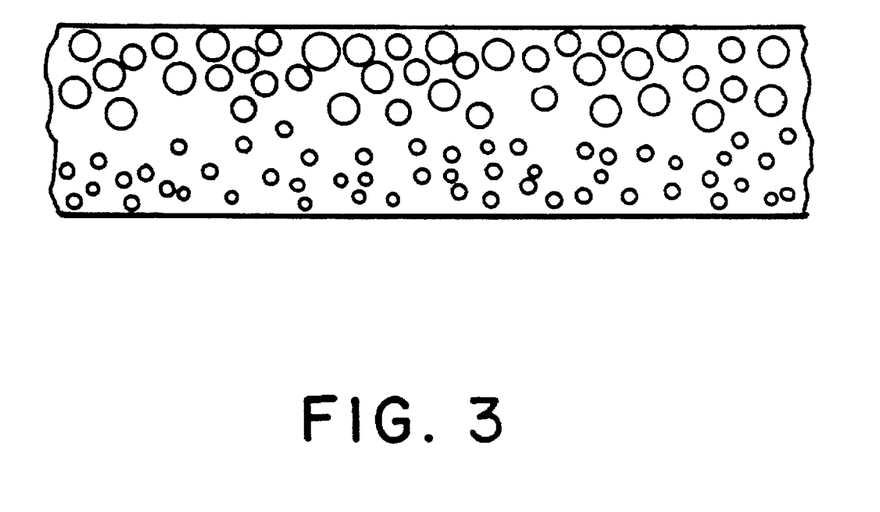
FIG. 3 is a cross-sectional view of one embodiment of an absorbent layer of the present invention.

When the absorbent layer comprises a relatively large concentration of superabsorbent particles, it is sometimes difficult for a liquid applied to one surface of the absorbent layer to pass through the absorbent layer to the other surface. In order to facilitate the passage of liquid through the absorbent layer, Applicants have found that it is beneficial to provide the absorbent layer with a Z-gradient (direction normal to the X-Y plane of the absorbent layer) particle size distribution. That is, if the high-absorbency material is in the form of particles or spheres having different maximum cross-sectional dimensions, it is desired to place the larger particles on the bodyside of the absorbent layer with the smaller particles located on the opposite side of the absorbent layer. Such a configuration is illustrated in FIG. 3 which is a cross-sectional view of an absorbent layer according to the present invention illustrating such a Z-gradient particle size distribution.

Test Methods

Absorbency Under Load

The Absorbency Under Load (AUL) is a test which measures the ability of an absorbent material to absorb a liquid (0.9 weight percent solution of sodium chloride in distilled water) while under an applied load or restraining force.

Figure 4:
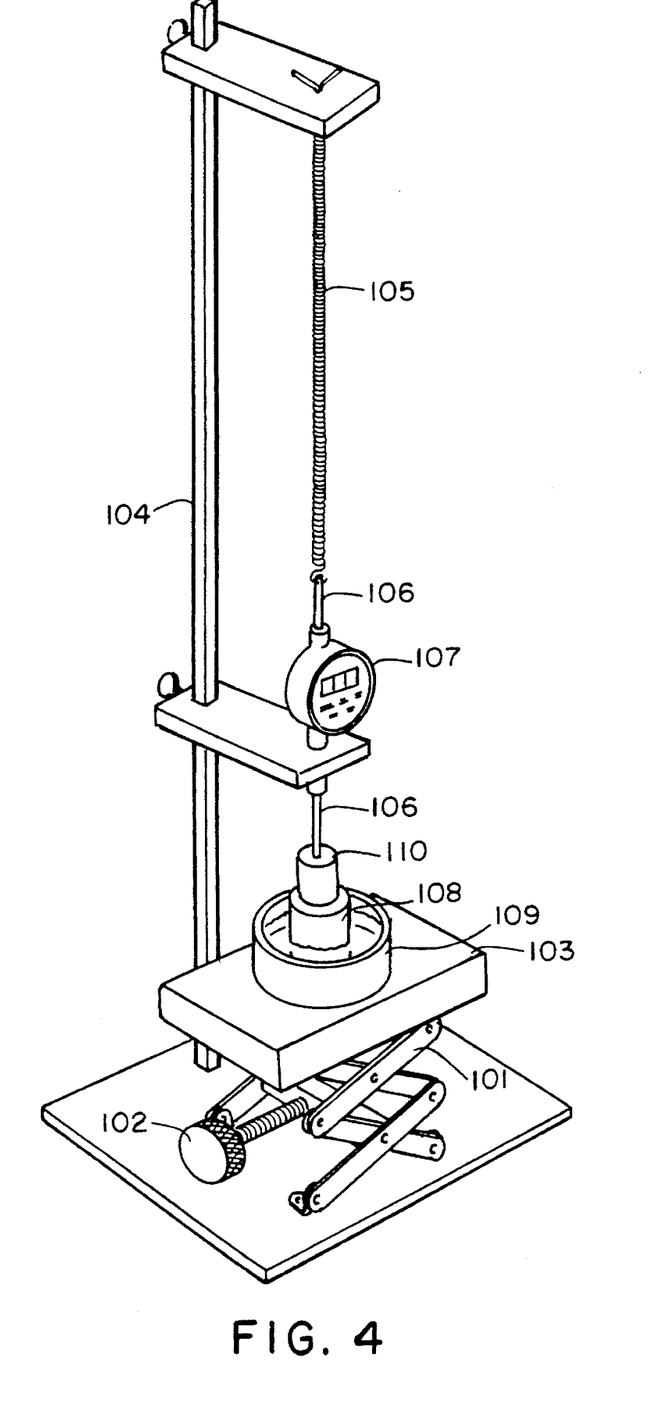
FIG. 4 illustrates the apparatus for determining the Absorbency Under Load values of a high-absorbency material.

Referring to FIG. 4, the apparatus and method for determining AUL will be described. Shown is a perspective view of the apparatus in position during a test. Shown is a laboratory jack 101 having an adjustable knob 102 for raising and lowering the platform 103. A laboratory stand 104 supports a spring 105 connected to a modified thickness meter probe 106, which passes through the housing 107 of the meter, which is rigidly supported by the laboratory stand. A plastic sample cup 108, which contains the high-absorbency (superabsorbent) material sample to be tested, has a liquid-permeable bottom and rests within a petri dish 109, which contains the saline solution to be absorbed. A weight 110 rests on top of a spacer disc (not visible) resting on top of the superabsorbent material sample (not visible).

The sample cup consists of a plastic cylinder having a 1 inch inside diameter and an outside diameter of 1.25 inch. The bottom of the sample cup is formed by adhering a 100 mesh metal screen having 150 micron openings to the end of the cylinder by heating the screen above the melting point of the plastic and pressing the plastic cylinder against the hot screen to melt the plastic and bond the screen to the plastic cylinder. Alternatively, the screen can be adhesively attached to the end of the cylinder. The modified thickness meter used to measure the expansion of the sample while absorbing the saline solution is a Mitutoyo Digimatic Indicator, IDC Series 543, Model 543-180, having a range of 0–0.5 inch and an accuracy of 0.00005 inch (Mitutoyo Corporation, 31–19, Shiba 5-chome, Minato-ku, Tokyo 108, Japan). As supplied from Mitutoyo Corporation, the thickness meter contains a spring attached to the probe within the meter housing. This spring is removed to provide a free falling probe, which has a downward force of about 27 grams. In addition, the cap over the top of the probe located on the top of the meter housing is also removed to enable attachment of the probe to the suspension spring 5 (available from McMaster-Carr Supply Co., Chicago, Ill., Item No. 9640K41), which serves to counter or reduce the downward force of the probe to about 1 gram, ±0.5 gram. A wire hook can be glued to the top of the probe for attachment to the suspension spring. The bottom tip of the probe is also provided with an extension needle (Mitutoyo Corporation, Part No. 131279) to enable the probe to be inserted into the sample cup.

To carry out the test, a 0.160 gram sample of the high-absorbency material, which has been sieved to a particle size between 300 and 600 microns, is placed into the sample cup. The sample is then covered with a plastic spacer disc, weighing 4.4 grams, which is slightly smaller than the inside diameter of the sample cup and serves to protect the sample from being disturbed during the test. The 100 grams weight is then placed on top of the spacer disc, thereby applying a load of 0.3 pound per square inch. The sample cup is placed in the petri dish on the platform of the laboratory jack which is raised up until it contacts the tip of the probe. The meter is zeroed. A sufficient amount of saline solution is added to the petri dish (50–100 milliliters) to begin the test. The distance the weight is raised by the expanding sample as it absorbs the saline solution is measured by the probe. This distance, multiplied by the cross-sectional area inside the sample cup, is a measure of the expansion volume of the sample due to absorption. Factoring in the density of the saline solution and the weight of the sample, the amount of saline solution absorbed is readily calculated. The weight of saline solution absorbed after 60 minutes is the AUL value, expressed as grams saline solution absorbed per gram of high-absorbency material. If desired, the readings of the modified thickness meter can be continuously input to a computer (Mitutoyo Digimatic Miniprocessor DP-2 DX) to make the calculations and provide AUL readings. As a cross-check, the AUL can also be determined by determining the weight difference between the sample cup before and after the test, the weight difference being the amount of solution absorbed by the sample.

Fluid Run-Off Evaluation

Figure 5:
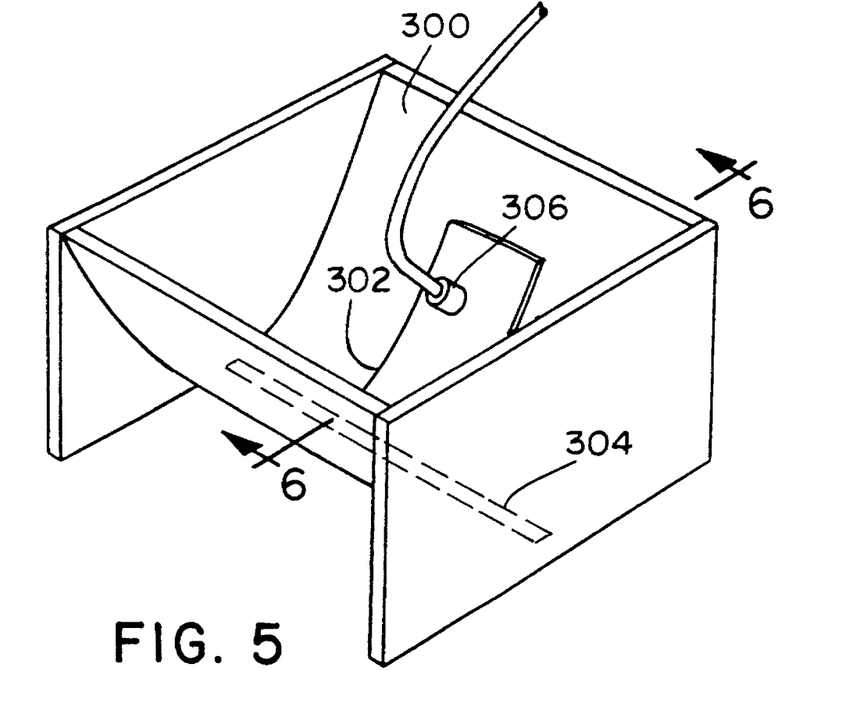
FIG. 5 is a perspective view of the apparatus used in conducting the fluid run-off determination.
Figure 6:
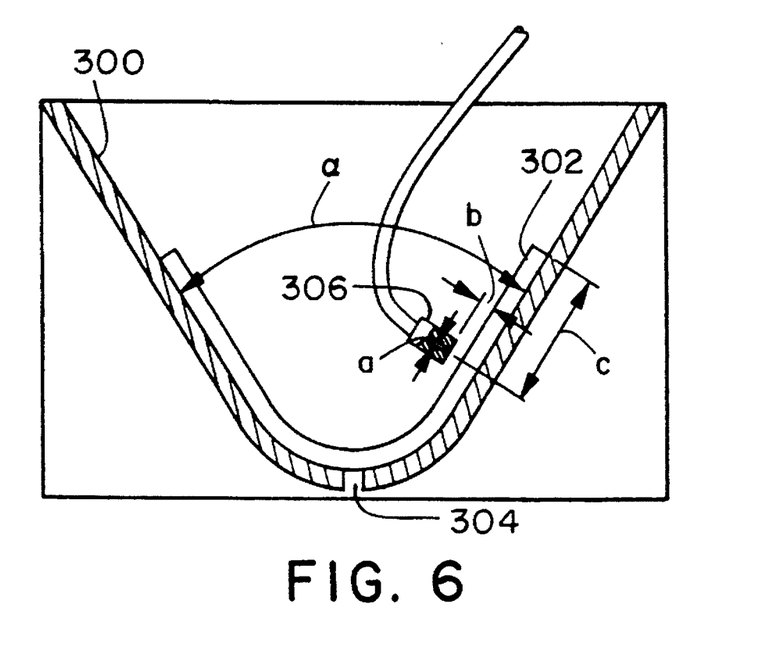
FIG. 6 is a cross-sectional view of the apparatus used in conducting the fluid run-off determination.

The fluid run-off evaluation of composites according to the present invention and comparative composites is determined as follows. Specifically, the fluid run-off is determined by providing a sample which is 15 inches long and 4.5 inches wide. Referring to FIG. 5, the sample 302 is placed in a trough 300 having an included angle (alpha) of 60 degrees. Trough 300 defines a slot 304 extending across the entire width of the trough 300 at its lowest point. The trough 300 is at least 4 inches wider than the sample 302 to be tested. A collection device (not pictured) is placed under trough 300 to collect fluid which passes out of trough 300 through slot 304. FIG. 6 is a cross-sectional view taken along line 6—6 of FIG. 5. As can be seen from reference to FIG. 6, test fluid is delivered to the sample 302 to be tested from a nozzle 306 having a 3 millimeter diameter (a) which is attached to a peristaltic pump equipped with a pulse suppressor. The nozzle is placed a distance (b) of 6.4 millimeters from the surface of the sample to be tested at a distance (c) of about 5.5 inches from the end of the sample to be tested such that the nozzle is generally perpendicular to the immediate adjacent surface of the sample 302 to be tested. This positioning should be maintained throughout the test. The sample to be tested is subjected to ten 60 milliliter insults of synthetic urine. The urine is applied through the nozzle 306 at a rate of approximately 15 millimeters per second and a velocity of about 210 centimeters per second. Each of the ten 60 milliliter insults is applied 15 minutes after the immediately preceding insult. The amount of fluid which passes through slot 304 and is collected in the collection device, is weighed (in grams), and is reported for each insult. As a general rule, the lower the amount of run-off per insult, the better the composite would be expected to perform in an absorbent product.

The synthetic urine composition referenced herein comprises 0.31 grams monobasic calcium phosphate monohydrate ($CaH_4(PO_4)_2H_2O$), 0.68 grams monobasic potassium phosphate ($KH_2PO_4$), 0.48 grams magnesium sulphate heptahydrate ($MgSO_47H_2O$), 1.33 grams potassium sulphate ($K_2SO_4$), 1.24 grams tribasic sodium phosphate dodecahydrate ($Na_3PO_412H_2O$), 4.4 grams sodium chloride (NaCl), 3.16 grams potassium chloride (KCl), 8.56 grams of urea ($(CO)NH_2)_2$), 0.1 grams pluronic 10R8 surfactant (a non-ionic surfactant commercially available from BASF Wyandotte Corporation) and 1 gram methyl paraben and 1 gram germall 115 preservative (commercially available from Santell Chemical Company, Chicago, Ill.) per liter using distilled water as a solvent. The components are added to 900 milliliters of distilled water in the order given and each dissolved before the next component is added. The solution is finally diluted to 1 liter. The solution is found to have a surface tension of 55 dynes per square centimeter.

Examples

The following materials are employed as first surge management layers.

Sample A — A bonded carded web formed from 60 weight percent of a 5.5 denier per filament polyester fiber commercially available from the Tennessee Eastman Company, Kingsport, Tenn., and 40 weight percent of a 2.25 denier per filament polyester fiber commercially available from Hoechst-Celanese, Spartansburg, S.C., under the trade designation T291. The bonded carded web is commercially available from Bonnar Fabrics, Greenville, S.C. The carded web formed from the fibers described above is bonded with 18 weight percent, based on total web weight, of a polyester binder powder commercially available from EMS-Chemie, Switzerland, under the trade designation EMS D1287 polyester binder powder. The bonded carded web has a basis weight of 50 grams per square meter and a density of about 0.044 grams per cubic centimeter.

Sample B — A bonded carded web formed from 60 weight percent of a 6.0 denier per filament polyester teraphthalate fiber commercially available from Hoechst-Celanese under the trade designation T295 and 40 weight percent of a 1.8 denier per filament sheath core (polyethylene sheath/polyethylene teraphthalate core) bicomponent fiber commercially available from BASF Corporation, Fibers Division, Williamsburg, Va., which carded web is bonded through a through-air bonding process. The web has a basis weight of about 50 grams per square meter and a density of about 0.044 grams per cubic centimeter.

Sample C — A fibrous web of side-by-side spunbond bicomponent fibers formed from polyethylene and polypropylene (50/50). The side-by-side bicomponent fibers have a thickness of 3.0 denier per filament. The spunbonded web is through-air bonded. The web has a basis weight of 54 grams per square meter and a density of 0.032 gram per cubic centimeter. The web is employed with the wire side up (closest to nozzle 306 during testing).

Sample D — A web is formed as described in connection with Sample C, except that the web is employed with the face side up.

Sample E — An air-formed web is formed comprising 50 weight percent of a 6.5 denier per filament polyethylene teraphthalate fiber commercially available from Tennessee Eastman under the trade designation Kodel® 431 and 50 weight percent of a 3.3 denier per filament polyethylene/polypropylene bicomponent fiber (polyethylene sheath/polypropylene core) fiber having a 6 millimeter length commercially available from Danaklon A/S, Denmark. The air-formed web is through-air bonded at a temperature sufficient to melt the polyethylene sheath of the bicomponent fiber. The web formed has a basis weight of 58 grams per square meter and a density of 0.026 gram per cubic centimeter.

Sample F — An airlaid web comprising 50 weight percent of wood pulp fluff fibers commercially available from Weyerhaeuser Company, Tacoma, Washington, under the trade designation NF-105, and 50 weight percent of a polypropylene meltblown fiber having a diameter of about 10 micrometers. The airformed web has a basis weight of about 75 grams per square meter and a density of about 0.048 grams per cubic centimeter.

Sample G — An airlaid web comprising wood pulp fluff and polypropylene meltblown fibers is formed as described above, except the web is formed to have a basis weight of 125 grams per square meter and a density of 0.05 grams per cubic centimeter.

The second surge management layer comprises an airlaid batt of wood pulp fluff commercially available from the Kimberly-Clark Corporation under the trade designation CR-54 (20 percent hardwood, 80 percent softwood). The airlaid batt has a basis weight of 115 grams per square meter and a density of 0.12 gram per cubic centimeter. The absorbent layer is formed comprising 70 weight percent of a high-absorbency superabsorbent material commercially available from Hoechst-Celanese under the trade designation IM-5000P; 17 weight percent of a wood pulp fluff commercially available from Kimberly-Clark Corporation under the trade designation CR-54; and about 13 weight percent water. The absorbent layer is airlaid on a cellulose wrap sheet having a basis weight of about 11 grams per square meter. A 4-inch wide strip of the wood pulp fluff, superabsorbent material, and water is formed on a 7-inch wide cellulose wrap sheet. A 3½-inch wide cellulose wrap sheet is laid on top of the mixture of fluff and superabsorbent with the extra width of the lower wrap sheet being folded over the edges of the mixture of fluff and superabsorbent to form a completely enclosed absorbent layer. The components of wood pulp fluff, superabsorbent material and water are formed on the lower wrap sheet in the following sequence: wood pulp fluff, superabsorbent material, and water. As formed, the superabsorbent particles having a larger particle diameter segregate on the side of the absorbent core nearest the 3½-inch wide cellulose wrap sheet. This side of the absorbent layer faces up. The absorbent layer has a basis weight of about 452 grams per square meter and a density of about 0.25 gram per cubic centimeter. After formation, the absorbent layer is allowed to come to equilibrium by being exposed to ambient conditions for a period of about 30 days.

In forming the composites of the present invention, a first surge management material selected from the samples described above is plied with an absorbent layer and the second surge management layer described above. The absorbent layer is located between the first surge management layer and the second surge management layer with the first surge management layer being located closest to nozzle 306 during testing. The 3-ply composites are then placed on a polyethylene film having a thickness of 1 mil and samples which are 15 inches long and 4 inches wide cut from the composites. The samples thus prepared are subjected to the fluid runoff evaluation test as described above. As the absorbent layer and second surge management layer are the same in each of the composites, the composites are identified by the first surge management material employed. It is understood that each of the samples comprise not only the first surge management layer but also an absorbent layer, a second surge management layer, and the lower polyethylene film backing. The results of the fluid runoff evaluation are set forth in Table 1.

improves the performance of the test composites in the fluid runoff evaluation test. Naturally, the lower the fluid runoff, the better the expected performance of the composite in an absorbent article such as a diaper. Moreover, it is seen that first surge management layers comprising a relatively high concentration of synthetic polymeric material fibers perform better than a first surge management layer comprising up to 50 weight percent of wood pulp fluff (without going to significantly higher basis weight).

Figure 7:
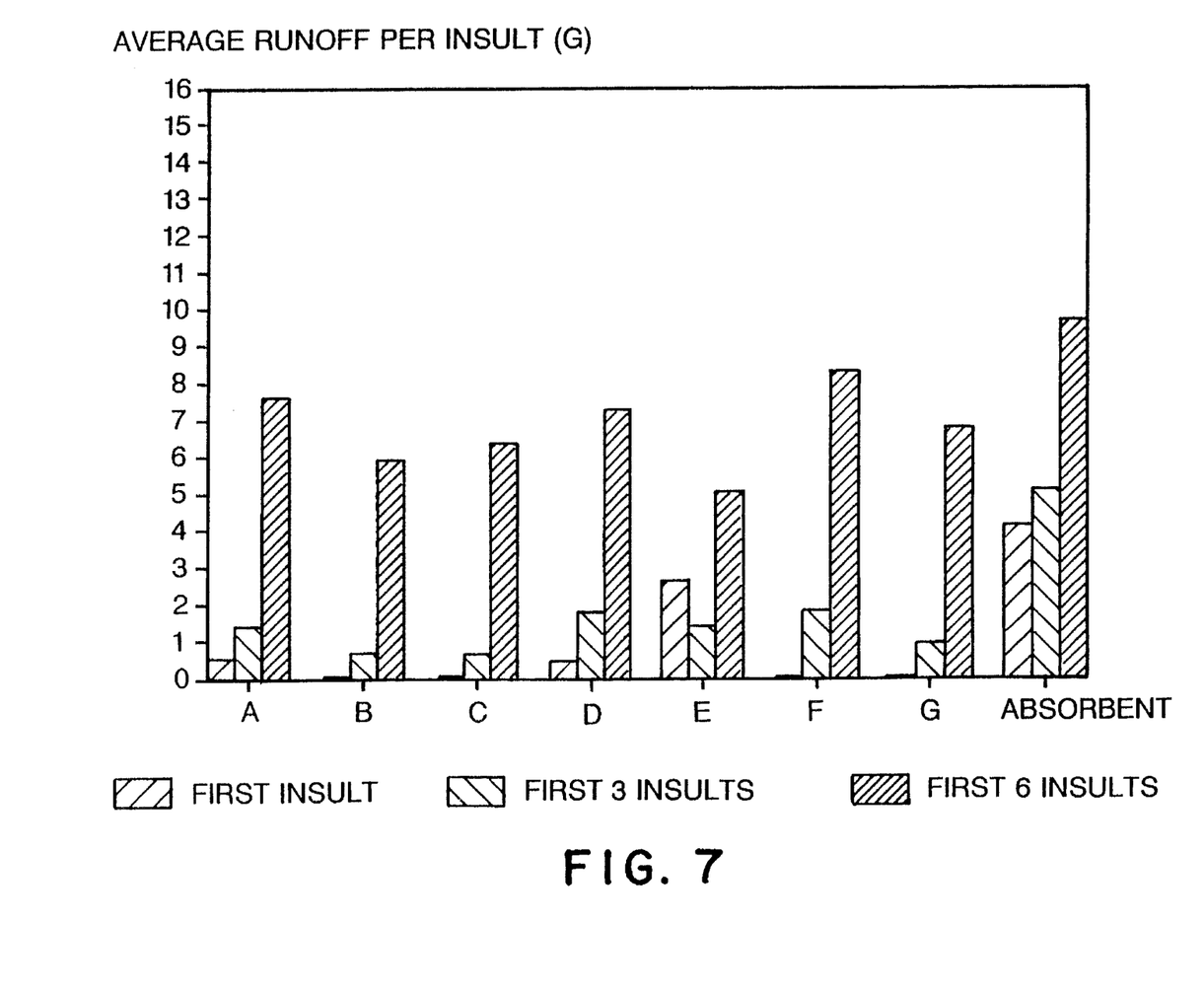
FIG. 7 graphically illustrates the results set forth in Table 1.
Figure 8:
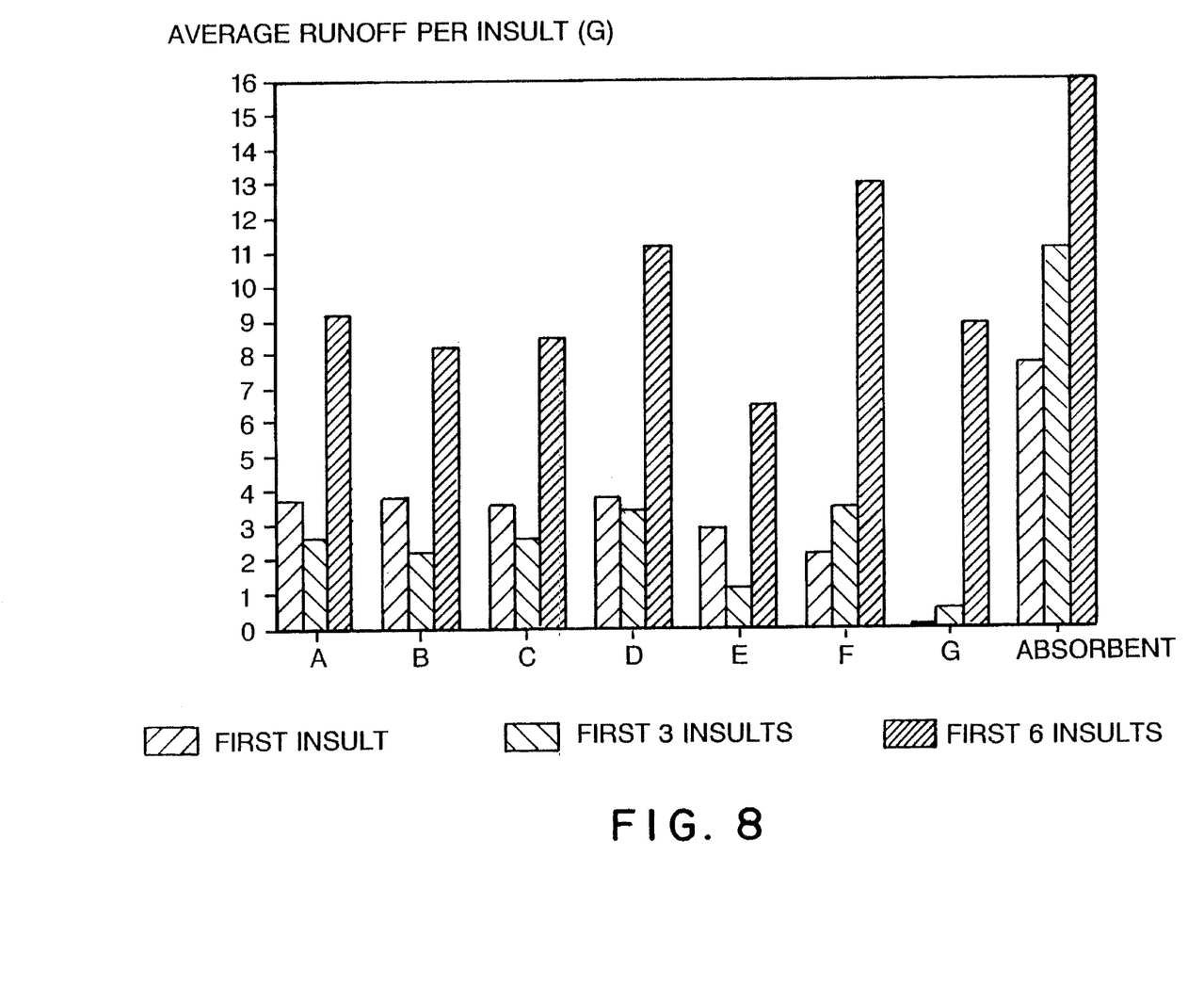
FIG. 8 graphically illustrates the results set forth in Table 2.

FIGS. 7 and 8 graphically illustrate the results set forth in Tables 1 and 2, respectively. As can be seen from reference to FIGS. 7 and 8, the various bar graphs represent the runoff for the first insult, and the average runoff per insult for the first three insults and the first six insults.

While the invention has been described in detail with respect to specific embodiments thereof, it will be appreciated that those skilled in the art, upon attaining an understanding of the foregoing, may readily conceive of alterations to, variations of, and equivalents to those embodiments. Accordingly, the scope of the present invention should be assessed as that of the appended claims and

TABLE 1

Runoff (grams)

| Sample | Insult No. | | | | | | | | | |
|---|---|---|---|---|---|---|---|---|---|---|
|  | 1 | 2 | 3 | 4 | 5 | 6 | 7 | 8 | 9 | 10 |
| A | 0.55 | 0.16 | 3.50 | 7.99 | 15.29 | 18.35 | 24.94 | 31.31 | 37.28 | 39.77 |
| B | 0.06 | 0.18 | 1.90 | 4.68 | 10.28 | 18.75 | 27.31 | 33.83 | 39.05 | 43.02 |
| C | 0 | 0 | 2.03 | 5.98 | 11.37 | 19.03 | 28.03 | 35.94 | 40.17 | 43.84 |
| D | 0.49 | 0.78 | 4.16 | 8.14 | 10.94 | 19.27 | 27.00 | 31.35 | 37.11 | 40.48 |
| E | 2.65 | 0 | 1.56 | 4.82 | 7.46 | 13.82 | 23.03 | 30.99 | 36.24 | 40.47 |
| F | 0.03 | 1.55 | 3.93 | 8.26 | 14.76 | 21.62 | 28.70 | 34.68 | 40.42 | 43.59 |
| G | 0 | 0.72 | 2.07 | 5.17 | 11.47 | 21.28 | 29.93 | 34.68 | 39.89 | 42.37 |
| Absorbent[1] | 4.12 | 4.58 | 6.59 | 9.67 | 14.06 | 18.94 | 25.10 | 30.17 | 32.94 | 38.67 |

[1]Absorbent layer and second surge management layer tested alone, with no first surge management layer.

For comparison purposes, the composites comprising a first surge management material from the materials described above, and an absorbent layer are formed on the polyethylene film backing. These composites do not comprise the second surge management layer and do not represent the present invention. These composites (also identified by the composition of the first surge management layer) are subjected to the fluid runoff evaluation test. The results are set forth in Table 2.

any equivalents thereto.

What is claimed is:

1. An absorbent structure, said absorbent structure comprising:

a first surge management layer comprising a fibrous web, said first surge management layer having a basis weight of from about 20 to about 200 grams per square meter, and a density of from about 0.01 to about 0.12 gram per cubic centimeter;

TABLE 2

Runoff (grams)

| Sample | Insult No. | | | | | | | | | |
|---|---|---|---|---|---|---|---|---|---|---|
|  | 1 | 2 | 3 | 4 | 5 | 6 | 7 | 8 | 9 | 10 |
| A | 3.71 | 0.76 | 3.50 | 9.03 | 15.43 | 22.67 | 29.77 | 34.06 | 38.16 | 42.86 |
| B | 3.82 | 0.25 | 2.61 | 7.32 | 14.19 | 21.15 | 28.84 | 35.52 | 39.83 | 43.13 |
| C | 3.59 | 0.85 | 3.36 | 7.23 | 12.93 | 23.09 | 29.58 | 36.05 | 40.01 | 43.06 |
| D | 3.79 | 1.62 | 4.94 | 10.31 | 18.56 | 27.95 | 34.05 | 36.74 | 40.55 | 40.93 |
| E | 8.04 | 1.79 | 2.66 | 7.60 | 13.77 | 20.85 | 28.83 | 34.31 | 39.44 | 43.16 |
| F | 2.15 | 1.85 | 6.54 | 14.69 | 22.32 | 30.34 | 35.65 | 39.15 | 43.59 | 46.04 |
| G | 0.02 | 0.11 | 1.59 | 8.28 | 17.14 | 26.08 | 32.50 | 37.47 | 41.97 | 45.21 |
| Absorbent[1] | 7.71 | 14.33 | 11.16 | 17.46 | 21.5 | 23.68 | 27.50 | 30.48 | 34.39 | 37.83 |

[1]Absorbent layer tested alone, with no first or second surge management layers.

As can be seen from reference to Tables 1 and 2, the presence of the second surge management layer greatly a second surge management layer comprising a fibrous web, said web comprising hydrophilic fibers, said second surge management layer having a basis weight of from about 20 to about 350 grams per square meter and a density of from about 0.04 to about 0.25 gram per cubic centimeter; and an absorbent layer located between and in liquid communication with said first and second surge management layers, said absorbent layer comprising means for containing a high-absorbency material and from about 50 to about 100 weight percent, based on total weight of said absorbent layer, of a high-absorbency material contained by said means for containing a high-absorbency material, said absorbent layer having a basis weight of from about 200 to about 1000 grams per square meter and a density of from about 0.06 to about 0.4 gram per cubic centimeter wherein the density of said absorbent layer is greater than the density of said first and second surge management layers and the density of the first surge management layer is different than the density of said second surge management layer.

2. The absorbent structure according to claim 1 wherein said first surge management layer is, in use, located between the body of a wearer and the absorbent layer.

3. The absorbent structure according to claim 1 wherein said first surge management layer comprises a nonsynthetic polymeric fiber.

4. The absorbent structure according to claim 3 wherein said first surge management layer is formed by a method selected from the group consisting of meltblowing, spunbonding, carding, and airlaying.

5. The absorbent structure according to claim 4 wherein said nonsynthetic polymeric fiber is selected from the group consisting of wood pulp fluff, cotton linters, cotton, and regenerated cellulose.

6. The absorbent structure according to claim 1 wherein said first surge management layer has a basis weight of from about 30 to about 150 grams per square meter.

7. The absorbent structure according to claim 1 wherein said second surge management layer comprises from 10 to 100 weight percent of hydrophilic fibers.

8. The absorbent structure according to claim 7 wherein said second surge management layer comprises 100 weight percent of cellulosic fibers.

9. The absorbent structure according to claim 1 wherein said second surge management layer has a basis weight of about 50 to about 200 grams per square meter.

10. The absorbent structure according to claim 1 wherein said absorbent layer comprises from about 60 to about 95 weight percent of a high-absorbency material contained by said means for containing a high-absorbency material.

11. The absorbent structure according to claim 10 wherein said absorbent layer comprises from about 70 to about 90 weight percent of a high-absorbency material contained by said means for containing a high-absorbency material.

12. The absorbent structure according to claim 1 wherein said absorbent layer has a basis weight of from about 250 to about 750 grams per square meter.

13. The absorbent structure according to claim 1 wherein the density of said absorbent layer is at least about 20 percent greater than the density of both of said first and second surge management layers.

14. The absorbent structure according to claim 13 wherein the density of said absorbent layer is at least about 30 percent greater than the density of both of said first and second surge management layers.

15. The absorbent structure according to claim 2 wherein the density of the first surge management layer is less than the density of the second surge management layer.

16. The absorbent structure according to claim 1 wherein the density of the first and second surge management layers differ by at least about 20 percent of the density of the lowest density layer.

17. The absorbent structure according to claim 1 wherein said absorbent layer defines holes.

18. The absorbent structure according to claim 1 wherein said absorbent layer comprises areas of reduced basis weight.

19. The absorbent structure according to claim 1 wherein said high absorbency material is in the form of particles or spheres having different maximum cross-sectional dimensions with the larger particles located on the side of the absorbent layer closest to a wearer in use.

20. An absorbent structure, said structure comprising a first surge management layer, said first surge management layer comprising a fibrous web, said fibrous web comprising nonsynthetic polymeric fibers, said first surge management layer having a basis weight of from about 30 to about 150 grams per square meter and a density of from about 0.015 to about 0.1 grams per cubic centimeter;

a second surge management layer, said second surge management layer comprising a fibrous web, said fibrous web comprising from about 55 to about 100 weight percent hydrophilic fibers, said second surge management layer having a basis weight of from about 50 to about 200 grams per square meter, and a density of from about 0.06 to about 0.16 grams per cubic centimeter; and an absorbent layer located between and in liquid communication with said first and second surge management layers, said absorbent layer comprising means for containing a high-absorbency material and from about 50 to about 100 weight percent, based on total weight of the absorbent layer, of a high-absorbency material contained by said means for containing a high-absorbency material, said absorbent layer having a basis weight of from about 250 to about 750 grams per square meter and a density of from about 0.12 to about 0.35 gram per cubic centimeter wherein the density of said absorbent layer is greater than the density of both of said first and second surge management layers, and the densities of the first and second surge management layers are different.

21. An absorbent product, said absorbent product comprising:

a liquid-impermeable bodyside liner;

a substantially liquid-impermeable outer cover; and an absorbent structure located between said liner and outer cover said absorbent structure comprising:

a first surge management layer comprising a fibrous web, said web comprising synthetic polymeric fibers, said first surge management layer having a basis weight of from about 20 to about 200 grams per square meter, and a density of from about 0.01 to about 0.12 grams per cubic centimeter;

a second surge management layer comprising a fibrous web, said web comprising hydrophilic fibers, said second surge management layer having a basis weight of from about 20 to about 350 grams per square meter and a density of from about 0.04 to about 0.25 gram per cubic centimeter; and an absorbent layer located between and in liquid communication with said first and second surge management layers, said absorbent layer comprising means for containing a high-absorbency material and from about 50 to about 100 weight percent, based on total weight of said absorbent layer, of a high-absorbency material contained by said means for containing a high-absorbency material, said absorbent layer having a basis weight of from about 200 to about 1000 grams per square meter and a density of from about 0.06 to about 0.4 gram per cubic centimeter wherein the density of said absorbent layer is greater than the density of said first and second surge management layers and the density of the first surge management layer is different than the density of said second surge management layer.

22. The absorbent product according to claim 21 wherein said first surge management layer is located between said bodyside liner and said absorbent structure.

23. An absorbent structure, said absorbent structure comprising:

a first surge management layer comprising a fibrous web, said web comprising nonsynthetic polymeric fibers, said first surge management layer having a basis weight of from about 20 to about 200 grams per square meter, and a density of from about 0.01 to about 0.12 gram per cubic centimeter;

a second surge management layer comprising a fibrous web, said web comprising hydrophilic fibers, said second surge management layer having a basis weight of from about 20 to about 350 grams per square meter and a density of from about 0.04 to about 0.25 gram per cubic centimeter; and an absorbent layer located between and in liquid communication with said first and second surge management layers, said absorbent layer comprising a fibrous web containing from about 50 to about 100 weight percent, based on total weight of said absorbent layer, of a high-absorbency material, said absorbent layer having a basis weight of from about 200 to about 1000 grams per square meter and a density of from about 0.06 to about 0.4 gram per cubic centimeter wherein the density of said absorbent layer is greater than the density of said first and second surge management layers and the density of the first surge management layer is different than the density of said second surge management layer.

* * * * *